United States Patent
Lu et al.

(10) Patent No.: US 12,285,486 B2
(45) Date of Patent: Apr. 29, 2025

(54) PHARMACEUTICAL COMPOSITION IN SOLID EXTRUDED FORM

(71) Applicants: SE Tylose USA, Inc., Plaquemine, LA (US); Shin-Etsu Chemical Co., Ltd., Tokyo (JP)

(72) Inventors: Jiannan Lu, East Hanover, NJ (US); Sakae Obara, Tokyo (JP)

(73) Assignees: SE Tylose USA, Inc; Shin-Etsu Chemical Co., Ltd., Tokyo (JP)

(*) Notice: Subject to any disclaimer, the term of this patent is extended or adjusted under 35 U.S.C. 154(b) by 0 days.

(21) Appl. No.: 17/134,668

(22) Filed: Dec. 28, 2020

(65) Prior Publication Data

US 2021/0113700 A1    Apr. 22, 2021

Related U.S. Application Data

(63) Continuation of application No. 16/046,488, filed on Jul. 26, 2018, now abandoned.

(60) Provisional application No. 62/541,928, filed on Aug. 7, 2017.

(51) Int. Cl.
| | |
|---|---|
| *A61K 9/16* | (2006.01) |
| *A61K 31/4418* | (2006.01) |
| *A61K 31/496* | (2006.01) |
| *A61K 47/26* | (2006.01) |
| *A61K 47/38* | (2006.01) |

(52) U.S. Cl.
CPC .......... *A61K 47/38* (2013.01); *A61K 31/4418* (2013.01); *A61K 31/496* (2013.01); *A61K 47/26* (2013.01)

(58) Field of Classification Search
CPC .. A61K 9/1682; A61K 9/1694; A61K 9/2054; A61K 9/2095; A61K 9/2077; A61K 9/2866
See application file for complete search history.

(56) References Cited

U.S. PATENT DOCUMENTS

| | | | |
|---|---|---|---|
| 11,090,295 B2 | 8/2021 | Maruyama | |
| 2005/0048112 A1* | 3/2005 | Breitenbach | A61P 31/18 514/370 |
| 2005/0163858 A1 | 7/2005 | Boehm | |
| 2008/0181948 A1* | 7/2008 | Berndl | A61P 31/12 424/484 |
| 2008/0189948 A1* | 8/2008 | Schulz-Harder | F28D 15/04 29/890.032 |
| 2012/0146255 A1* | 6/2012 | Maschke | A61K 9/1694 264/210.1 |
| 2013/0303628 A1* | 11/2013 | Breitenbach | A61K 9/146 514/679 |
| 2014/0086993 A1 | 3/2014 | Guth et al. | |
| 2015/0044289 A1 | 2/2015 | Maruyama | |
| 2016/0120869 A1 | 5/2016 | Leutner | |

FOREIGN PATENT DOCUMENTS

| | | |
|---|---|---|
| CN | 103237458 | 8/2013 |
| JP | 2014-503470 A | 2/2014 |
| JP | 6162662 | 6/2017 |
| WO | 2008037809 | 4/2008 |
| WO | 2008067164 | 6/2008 |
| WO | 2009016358 | 2/2009 |
| WO | 2011039369 | 4/2011 |
| WO | WO-2012049253 A1 * | 4/2012 ............. A23L 33/00 |

OTHER PUBLICATIONS

Decision of Rejection, Japanese Patent Application No. 2020-507690, Aug. 5, 2021.
Decision of Rejection, English Translation, Japanese Patent Application No. 2020-507690, Aug. 5, 2021.
International Preliminary Report on Patentability dated Feb. 11, 2020 in PCT/US2018/044311.
National Intellectual Property Administration, P.R. China, Chinese Office Action for Patent Application No. CN 201888051506.1, Dec. 9, 2022.
European Patent Office, Examination Report for European Patent Application No. 18 753 036.5-1109, Aug. 23, 2022.
Intellectual Property Office, Office Action for KR Patent Application No. 10-2020-7003705, Apr. 18, 2023.
Intellectual Property India, First Examination Report (FER) for India Patent Application No. 202328005192, May 9, 2023.
The Korean Intellectual Property Office, Office Action for KR 10-2020-7003705, Oct. 17, 2023.
European Patent Office, Examination Report for International Patent Application No. EP18753036.5, Mar. 28, 2024.
Korean Intellectual Property Office, Korean Office Action for International Patent Application No. KR 10-2024-7022574, Aug. 1, 2024.

* cited by examiner

*Primary Examiner* — Micah Paul Young
(74) *Attorney, Agent, or Firm* — Williams Mullen; F. Michael Sajovec

(57) ABSTRACT

A pharmaceutical composition including an extruded solid and one or more pharmaceuticals or nutraceuticals is provided. The extruded solid includes hydroxypropylmethylcellulose acetate succinate and isomalt.

17 Claims, 3 Drawing Sheets

US 12,285,486 B2

PHARMACEUTICAL COMPOSITION IN SOLID EXTRUDED FORM

RELATED APPLICATION

The present application is a continuation application of U.S. application Ser. No. 16/046,488, filed Jul. 26, 2018, which claims priority from U.S. Provisional Application No. 62/541,928 filed Aug. 7, 2017, the disclosures of which are incorporated herein by reference in their entireties.

FIELD OF THE INVENTION

The present invention relates to a pharmaceutical composition in a solid extruded form wherein extrusion may be at a lower temperature and the resulting extrudate has a higher compressibility.

BACKGROUND OF THE INVENTION

Many pharmaceuticals and nutraceuticals are provided in a solid form using melt extrusion process. Generally, an extruder comprises a barrel with screws that force the materials including a polymeric material and the active pharmaceutical ingredient (API) through a shaping die. The extruder is typically heated to soften the polymeric material and to lower its melt viscosity. Such a melt extrusion process is often used to formulate poorly soluble APIs as solid dispersions. In the process, the non-active polymer is often in the amorphous state or semi-crystalline state and the API is converted to its amorphous state from its initial crystalline state to enhance its solubility. Once extruded the solid form is typically milled and then compressed into a tablet, pellet or granule.

Viscosity is an important aspect of melt extrusion and is often reduced by increasing heat. Many APIs, however, are heat sensitive, thus excessive heat must be avoided to prevent adversely affecting the activity of the API. After extrusion, compressibility is an important aspect, and the solid form must be sufficiently hard to be able to compress the extrudate into its desired form.

Thus, the present invention provides a pharmaceutical composition exhibiting a lower melt viscosity and a solid extruded from (extrudate) exhibiting a higher compressibility.

SUMMARY OF THE INVENTION

A pharmaceutical composition is provided and includes an extrudable solid and one or more pharmaceuticals or nutraceuticals. The extrudable solid comprises hydroxypropyl-methylcellulose acetate succinate and isomalt.

DETAILED DESCRIPTION OF EMBODIMENTS OF THE INVENTION

Figure 1:
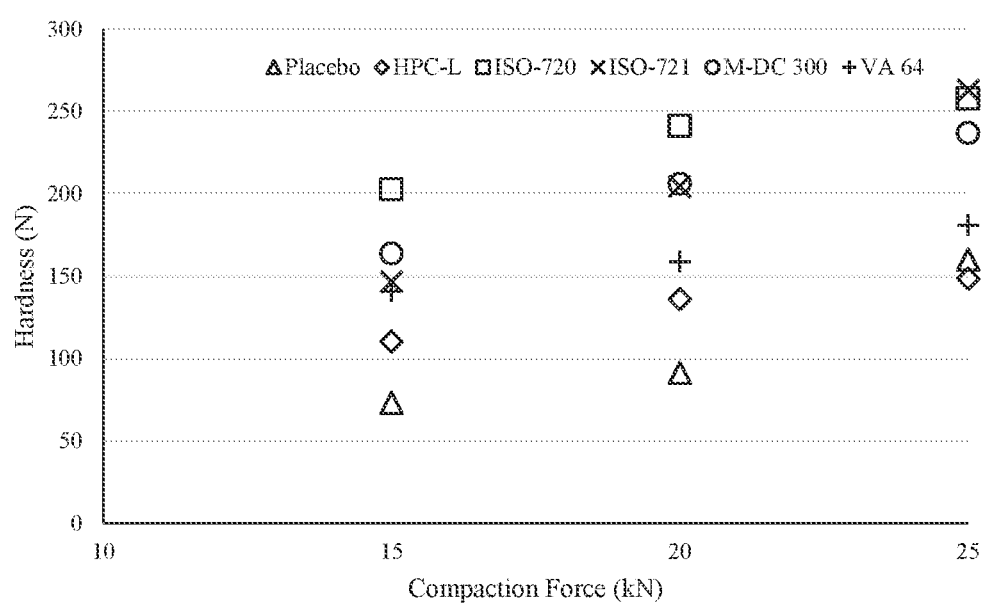
FIG. 1 illustrates tablet hardness using a TBH 125 (Erweka) tester in accordance with Example 1.

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

The term "consists essentially of" (and grammatical variants), as applied to in this invention, means the methods or compositions can contain additional steps or components as long as the additional steps or components do not materially alter the basic and novel characteristic(s) of the present invention.

The term "consisting of" excludes any additional step or component that is not specified in the claim.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

All patents, patent applications and publications referred to herein are incorporated by reference in their entirety. In case of a conflict in terminology, the present specification is controlling.

As one of ordinary skill in the art may appreciate, the parameters described herein may vary greatly depending on the process, and/or formulation as well as the desired properties of the final product.

The present invention is directed to a novel pharmaceutical composition comprising an extrudable solid (i.e., an extrudate) and a pharmaceutical or nutraceutical mixed with the extrudable solid. The extrudable solid comprises hydroxypropylmethylcellulose acetate succinate (HPMCAS) and isomalt.

In one embodiment, the HPMCAS is commercially available such as Shin-Etsu AQOAT® from Shin-Etsu Chemical Co., Ltd. (Japan), AffiniSol® from Dow Chemical (USA), and AquaSolve™ from Ashland (USA). In one embodiment, the isomalt is galenIQ™ available from BENEO GmbH (Germany). Isomalt is a sugar alcohol comprising an equal mixture of two stereoisomers, α-glucopyranosyl-1-1-D-mannitol (GPM) and α-D-glucopyranosyl-1, 6-D-sorbitol (GPS).

Optionally, other materials typically used as additives or excipients in pharmaceutical or nutraceutical compositions may be included. Exemplary other components include control release agents such as hypromellose, hydroxypropyl cellulose, ethylcellulose, hydroxypropylmethylcellulose phthalate, cellulose acetate phthalate, carboxymethylethylcellulose, methyl methacrylate-methacrylate copolymer, methacrylate-ethyl acrylate copolymer, methacrylate-methyl acrylate-methyl methacrylate copolymer, polyvinyl acetate phthalate and shellac. These other components may be included in amounts of about 1 to about 50 percent by weight of the composition.

The extrudable solid composition to be extruded comprises about 10 to about 80 percent HPMCAS, about 3 to 50 percent isomalt and about about 10 to about about 80 percent API. The extrudate (tablet) comprises about 10 to about 100 percent of the extrudable solid composition for extrusion, about 0 to about 20 percent of a disintegrant, about 0 to about 80 percent filler, about 0 to about 80 percent binder and about 0 to about 1 percent lubricant/glidant.

Suitable disintegrants include hydroxypropylcellulose (HPC), low-substituted HPC (L-HPC), carboxymethylcellulose (CMC), sodium CMC, calcium CMC, crospovidone, croscarmellose sodium; starches (e.g., carboxymethyl starch, hydroxylpropyl starch, modified starch); crystalline cellulose, sodium starch glycolate; alginic acid or a salt thereof, such as sodium alginate or their equivalents and mixtures thereof.

Suitable fillers include lactose, lactose monohydrate, lactitol, saccharose, sorbitol, mannitol, dextrates, dextrins, dextrose, maltodextrin, croscarmellose sodium, silicified microcrystalline cellulose, microcrystalline cellulose, hydroxypropylcellulose, low-substituted hydroxypropylcellulose, hydroxypropylmethylcellulose polymers, hydroxyethylcellulose, sodium carboxymethylcellulose, carboxymethylene, carboxymethyl hydroxyethylcellulose and other cellulose derivatives, starches or modified starches (including potato starch, corn starch, maize starch and rice starch) and mixtures thereof.

Suitable binders include polyvinyl pyrrolidone (also known as povidone), polyethylene glycol(s), acacia, alginic acid, agar, calcium carrageenan, cellulose derivatives such as ethyl cellulose, methyl cellulose, hydroxypropyl cellulose, hydroxypropyl methyl cellulose, sodium carboxymethylcellulose, dextrin, gelatin, gum arabic, guar gum, tragacanth, sodium alginate, or mixtures thereof or any other suitable binder.

Suitable lubricants/glidants include stearic acid and pharmaceutically acceptable salts or esters thereof (for example, magnesium stearate, calcium stearate, sodium stearyl fumarate or other metallic stearates), talc, microcrystalline waxes, glycerides, light mineral oil, polyethylene glycol, silica acid and pharmaceutically acceptable salts or esters thereof (for example, silicates, silicon dioxide, colloidal silicon dioxide, sucrose esters of fatty acids, hydrogenated vegetable oils (for example, hydrogenated castor oil), or mixtures thereof.

The overall composition may include about 65 to about 95 percent by water weight as the dispersing agent to provide the composition in aqueous form.

Other additives may include absorption enhancers, dissolution modifying agents, coloring aids, flavoring agents, and stabilizing agents (e.g., dibasic sodium phosphate).

The extruded form may be formed into tablets, pellets and granules.

In operation, the API may be blended with the hydropropylmethylcellulose acetate succinate and isomalt in a high-speed blender for 0 to 60 minutes. The blend may be extruded in one embodiment through a twin-screw extruder at a temperature of 100° to 200° C. and a screw speed of 100 to 1000 rpm. Specific shaping of the extrudate may occur as will be known to one skilled in the art. The extrudate may then be compressed into a tablet, pellet or granule using conventional tableting machines. The resulting tablet, pellet or granule may optionally then be coated using conventional coating equipment to improve the appearance or taste or film-coated with an aqueous or organic polymer composition.

The active pharmaceutical ingredient (API) may be a pharmaceutical or a nutraceutical. As used herein "pharmaceutical" is defined as any chemical substance intended for use in the medical diagnosis, cure, treatment, or prevention of disease, for example over-the-counter drugs (OTC) and prescription only medicine (POM). Exemplary active pharmaceutical components are listed in U.S. Pat. No. 6,723,358, column 9, line 25 to column 13, line 25, the disclosure of which is incorporated herein by reference in its entirety.

As used herein "nutraceutical" supplement include any nutrients that may provide health and medical benefits, including the prevention and treatment of disease. Examples include, but are not limited to, vitamins, minerals, probiotics, enzymes, herb and other botanical extracts, amino acid, concentrates, metabolites, constituents, etc.

Exemplary vitamins and minerals include, but are not limited to, vitamins A (in the form of, for example, palmitate or beta carotene), B-complex (such as B-1, B-2, B-6 and B-12), C, D, E and K; niacin; acid vitamins such as pantothenic acid and folic acid; biotin; minerals such as iron, calcium, magnesium, iodine, copper, phosphorus, zinc, manganese, potassium, chromium, cobalt, molybdenum, selenium, nickel, tin, silicon, vanadium and boron; nutraceutical supplements such as fluorine and chlorine; and the like. Various herbs and herbal remedies may be utilized as the nutraceutical supplements. The herbs are generally selected from those that have various medicinal or dietary supplement properties. Herbs are generally aromatic plants or plant parts that can be used medicinally or for flavoring. Examples include Gingko biloba, gotu kola, echinacea, St. John's wort, ginseng, valerian and the like. Suitable herbs may be used alone or in various mixtures in the filling described herein.

The present invention will be further illustrated by the following non-limiting examples.

EXAMPLE 1

The extrudate was prepared by blending HPMCAS (Shin-Etsu AQOAT® AS-MMP), isomalt and the API (nifedipine) for 20 minutes. Isomalt 720 and Isomalt 721 available GalenIQ™ from Beneo, Germany was added at 5, 10 and 20 percent levels.

Mannitol (Pearlitol®), hydropropylcellulose (grade: HPC-L) and copovidone (Kollidon®) were used as comparative additives to isomalt. A control without isomalt or the other additives was also prepared.

Each was tested for percentage of maximum torque during an extrusion process. The extruder was a Pharma-11 twin-screw extruder (Thermo Scientific, Germany), at the main barrel temperature of 175° C. The results are provided in Table 1.

TABLE 1

Percentage of Maximum Torque during Extrusion Process

| Additive | Amount Added | | |
|---|---|---|---|
| | 5% | 10% | 20% |
| Isomalt 720 | 41 | 22 | 16 |
| Isomalt 721 | 37 | 20 | 13 |
| HPC-L | 45 | 45 | 39 |
| Copovidone | 43 | 43 | 45 |
| Mannitol | 40 | 33 | 29 |

The control with no additive had a 58% maximum torque.

Figure 2:
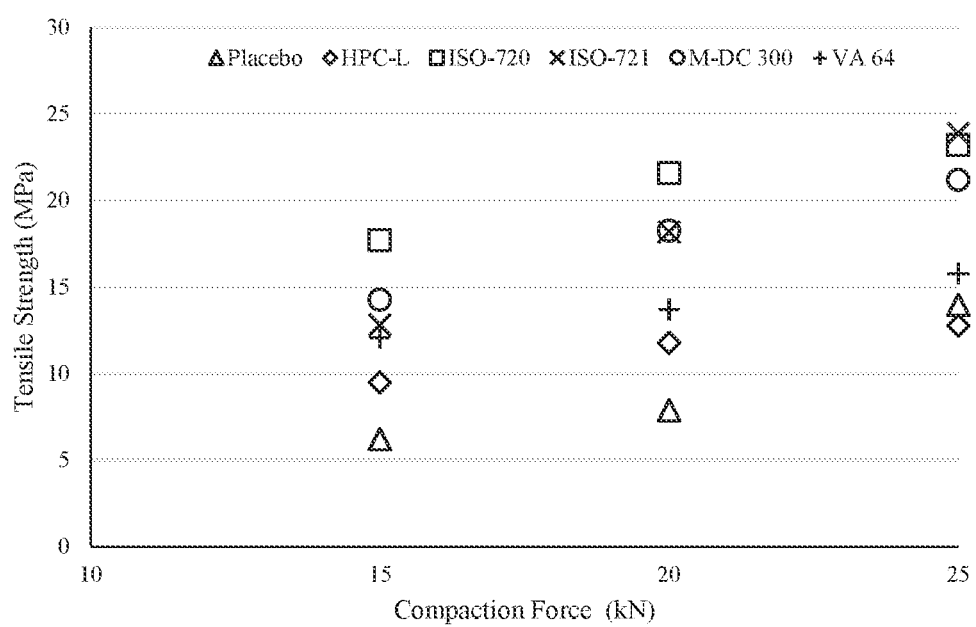
FIG. 2 illustrates tensile strength in accordance with Example 1.

The extrudable composition including 20 percent added were compressed at 15, 20 or 25 KN using a Handtab-200 single station table press (Ichihashiseki, Japan). Tablet hardness was recorded using a TBH 125 (Erweka, Germany) hardness tester. The results are provided in FIG. 1. Tensile strength was further calculated and is shown in FIG. 2.

EXAMPLE 2

Using a Pharma-11 twin-screw extruder (Thermo Scientific, Germany), a mixture of API (nifedipine) (20%) HPMCAS (AS-MMP, 75 or 60%) and Isomalt 720 (5 or 20%) was extruded. The main barrel temperature was set at 155° C. or 175° C., and screw speed was set at 100 or 400 rpm. The parameters were set according to $2^3$ factorial Plackett-Burman design to carry out 12 experiments. The extrudate was milled and compressed into a tablet using a single-punch tablet press (Handtab-200, Ichihashiseki, Japan) at 25 kN, and hardness was measured using a TBH 125 hardness tester (Erweka, Germany). The results are summarized in Table 2.

TABLE 2

Effect of Processing Parameter and Isomalt on Tensile Strength of Tablets

| Experimental Number | Screw Speed (rpm) | Main Barrel Temperature (° C.) | Isomalt (%) | Tensile Strength of Tablet (MPa) |
|---|---|---|---|---|
| 1 | 100 | 155 | 20 | 18.91 |
| 2 | 100 | 155 | 5 | 10.12 |
| 3 | 400 | 155 | 20 | 14.94 |
| 4 | 400 | 155 | 5 | 14.72 |
| 5 | 400 | 175 | 5 | 16.84 |
| 6 | 400 | 175 | 20 | 24.64 |
| 7 | 100 | 175 | 20 | 22.19 |
| 8 | 100 | 175 | 5 | 17.81 |
| 9 | 100 | 155 | 20 | 25.99 |
| 10 | 100 | 155 | 5 | 16.39 |
| 11 | 400 | 175 | 5 | 15.15 |
| 12 | 400 | 175 | 20 | 24.92 |

The results clearly indicate that higher content of isomalt provides higher tensile strength.

EXAMPLES 3A AND 3B

Figure 3:
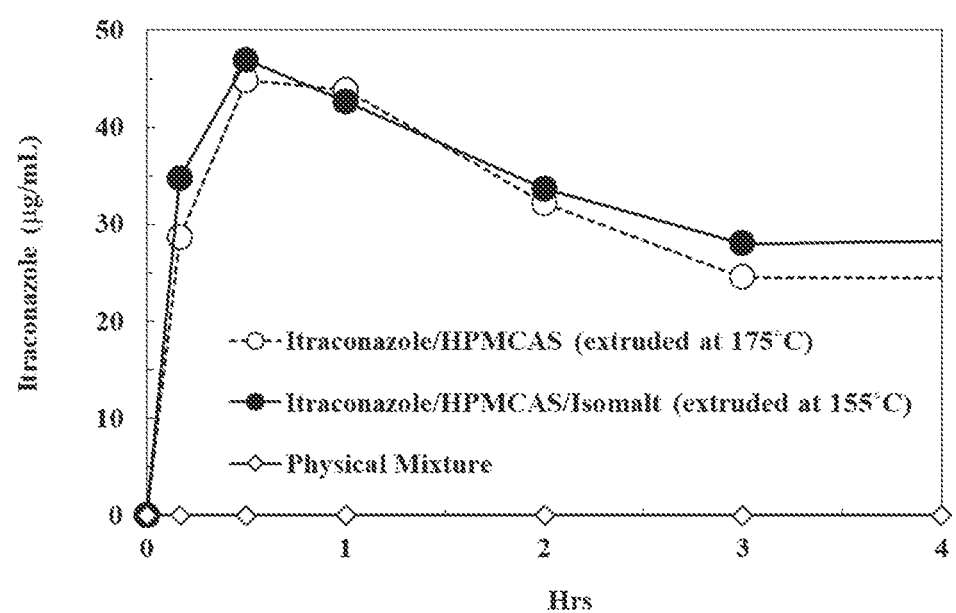
FIG. 3 illustrates dissolution test results in accordance with Examples 3A and 3B.

Using a Pharma-11 twin-screw extruder (Thermo Scientific, Germany), a mixture of API (itraconazole (20%)) and HPMCAS (AS-MMP, 80%) was extruded at the main barrel temperature of 175° C. (Example 3A). The extrudate was milled and compressed into tablets (diameter: 1 cm, weight: 400 mg) using a single-punch tablet press (Handtab-200, Ichihashiseki, Japan) at a compression force of 8 kN. The tablet hardness measured using a TBH 125 hardness tester (Erweka, Germany), was 90N. In the same way, a mixture of API (itraconazole (20%)), HPMCAS (AS-MMP, 65%), and Isomalt 721 (15%) was extruded (Example 3B). The main barrel temperature of 155° C. was necessary to achieve the same extruding torque as the extrusion without isomalt. The tablet hardness was 230N, which was significantly higher than the formulation without isomalt. Dissolution test for both tablets of Examples 3A and 3B was carried out using a dissolution tester (Model 2500, Distek, USA). The analysis of itraconazole was done using an Agilent 1100 HPLC (USA). The dissolution results are shown in FIG. 3. FIG. 3 illustrates that the dissolution pattern for both tablets of Examples 3A and 3B are identical and both have significantly better dissolution compared to the mere physical mixture of the ingredients. This clearly indicates that isomalt has benefits in the processing and performance of HPMCAS solid dispersion by melt extrusion, without providing any substantial negative effect to the dissolution of the API.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

That which is claimed:

1. An extrusion process for forming a tablet, a pellet or granule, the process comprising:
    forming an extrudable composition by forming a pharmaceutical composition consisting essentially of one or more pharmaceuticals or nutraceuticals, hydroxypropylmethyl cellulose acetate succinate, and 20 to 50 percent of isomalt
    extruding the extrudable composition at a temperature of 100° to 200° C. to form an extrudate and;
    compressing the extrudate into a tablet, a pellet or granule to provide a tablet, a pellet or a granule having improved tensile strength and hardness as compared to the pharmaceutical composition comprising hydroxypropylmethyl cellulose acetate succinate without 20 to 50 percent isomalt.

2. The extrusion process of claim 1, wherein the extrudable solid is extruded through a twin-screw extruder.

3. The extrusion process of claim 2, wherein the extrudable solid is extruded at a screw speed of 100 to 1000 rpm.

4. The extrusion process of claim 1, wherein the one or more pharmaceuticals or nutraceuticals, hydroxypropylmethyl cellulose acetate succinate and isomalt are blended in a high-speed blender for 0 to 60 minutes.

5. The extrusion process of claim 4 further including coating the tablet, the pellet or the granule with an aqueous or organic polymer composition.

6. The extrusion process of claim 1, wherein a control release agent is blended with the one or more pharmaceuticals or nutraceuticals, hydroxypropylmethyl cellulose acetate succinate and isomalt.

7. The extrusion process of claim 6, wherein the control release agent is selected from the group consisting of hypromellose, hydroxypropyl cellulose, ethylcellulose, hydroxypropylmethylcellulose phthalate, cellulose acetate phthalate, carboxymethylethylcellulose, methyl methacrylate-methacrylate copolymer, methacrylate-ethyl acrylate copolymer, methacrylate-methyl acrylate-methyl methacrylate copolymer, polyvinyl acetate phthalate and shellac.

8. The extrusion process of claim 1, wherein a disintegrant is blended with the one or more pharmaceuticals or nutraceuticals, hydroxypropylmethyl cellulose acetate succinate and isomalt.

9. The extrusion process of claim 8, wherein the disintegrant is selected from the group consisting of hydroxypropylcellulose, low-substituted hydroxypropylcellulose, carboxymethylcellulose, sodium carboxymethylcellulose, calcium carboxymethylcellulose, crospovidone, croscarmellose sodium, starches; crystalline cellulose, sodium starch glycolate, and alginic acid or a salt thereof.

10. The extrusion process of claim 1, wherein a filler is blended with the one or more pharmaceuticals or nutraceuticals, hydroxypropylmethyl cellulose acetate succinate and isomalt.

11. The extrusion process of claim 10, wherein the filler comprises lactose, lactose monohydrate, lactitol, saccharose, sorbitol, mannitol, dextrates, dextrins, dextrose, maltodextrin, croscarmellose sodium, silicified microcrystalline cellulose, microcrystalline cellulose, hydroxypropylcellulose, low-substituted hydroxypropylcellulose, hydroxypropylmethylcellulose polymers, hydroxyethylcellulose, sodium carboxymethylcellulose, carboxymethylene, and carboxymethyl hydroxyethylcellulose and mixtures thereof.

12. The extrusion process of claim 1, wherein a binder is blended with the one or more pharmaceuticals or nutraceuticals, hydroxypropylmethyl cellulose acetate succinate and isomalt.

13. The extrusion process of claim 12, wherein the binder is selected from the group consisting of polyvinyl pyrrolidone, polyethylene glycol, acacia, alginic acid, agar, calcium carrageenan, cellulose derivatives, dextrin, gelatin, gum arabic, guar gum, tragacanth, sodium alginate, and mixtures thereof.

14. The extrusion process of claim 1, wherein a lubricant is blended with the one or more pharmaceuticals or nutraceuticals, hydroxypropylmethyl cellulose acetate succinate and isomalt.

15. The extrusion process of claim 14, wherein the lubricant is selected from the group consisting of stearic acid and pharmaceutically acceptable salts or esters thereof, talc, microcrystalline waxes, glycerides, light mineral oil, polyethylene glycol, silica acid and pharmaceutically acceptable salts or esters thereof, and mixtures thereof.

16. The extrusion process of claim 1, wherein the extrudable solid further comprises
   c) 0.1 to 20 percent of a disintegrant;
   d) 0.1 to 80 percent of a filler;
   e) 0.1 to 80 percent of a binder; and
   f) 0.1 to 1 percent of a lubricant.

17. An extrusion process comprising:
   forming a pharmaceutical composition consisting essentially of one or more pharmaceuticals or nutraceuticals, hydroxypropylmethyl cellulose acetate succinate and 20 percent to 50 percent of isomalt by blending the composition in a high-speed blender for 0 to 60 minutes to form an extrudable solid;
   extruding the extrudable solid through a twin-screw extruder at a temperature of 100° to 200° C. and a screw speed of 100 to 1000 rpm to form an extrudate; and
   compressing the extrudate into a tablet, a pellet or granule having improved tensile strength and hardness as compared to the pharmaceutical composition comprising hydroxypropylmethyl cellulose acetate succinate without 20 to 50 percent isomalt.

* * * * *